(12) United States Patent
Huebner et al.

(10) Patent No.: US 9,707,022 B2
(45) Date of Patent: Jul. 18, 2017

(54) BONE PLATE SUPPORTED BY A LEG MEMBER AND USED AS A LEVER

(71) Applicant: Acumed LLC, Hillsboro, OR (US)

(72) Inventors: Randall J. Huebner, Portland, OR (US); Joshua P. Federspiel, Portland, OR (US); Carol-Lynn E. Connors, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 15/237,449

(22) Filed: Aug. 15, 2016

(65) Prior Publication Data

US 2016/0346020 A1    Dec. 1, 2016

Related U.S. Application Data

(63) Continuation of application No. 13/652,185, filed on Oct. 15, 2012, now Pat. No. 9,414,871, which is a continuation-in-part of application No. 13/246,684, filed on Sep. 27, 2011, now Pat. No. 8,425,575.

(60) Provisional application No. 61/386,925, filed on Sep. 27, 2010.

(51) Int. Cl.
*A61B 17/80* (2006.01)
*A61B 17/88* (2006.01)
*A61B 6/12* (2006.01)
*A61B 6/00* (2006.01)
(Continued)

(52) U.S. Cl.
CPC ........ *A61B 17/808* (2013.01); *A61B 17/8014* (2013.01); *A61B 17/8052* (2013.01); *A61B 17/8061* (2013.01); *A61B 17/8085* (2013.01); *A61B 17/8866* (2013.01); *A61B 6/12* (2013.01); *A61B 6/487* (2013.01); *A61B 17/1782* (2016.11);
(Continued)

(58) Field of Classification Search
CPC ............ A61B 17/1728; A61B 17/8019; A61B 17/808
See application file for complete search history.

(56) References Cited

U.S. PATENT DOCUMENTS

| | | | |
|---|---|---|---|
| 2,737,835 A | | 3/1956 | Herz |
| 5,182,996 A | * | 2/1993 | Gutgsell .............. A47B 87/002 108/64 |
| 5,613,969 A | | 3/1997 | Jenkins, Jr. |

(Continued)

FOREIGN PATENT DOCUMENTS

WO        2010149702 A1    12/2010

OTHER PUBLICATIONS

U.K. Intellectual Property Office, "Patents Act 1977: Combined Search and Examination Report Under Sections 17 and 18(3)" in connection with related U.K. Application No. GB1116591.7, dated Dec. 23, 2011, 5 pages.

(Continued)

*Primary Examiner* — Anu Ramana
(74) *Attorney, Agent, or Firm* — Kolisch Hartwell, P.C.

(57) ABSTRACT

System, including apparatus and methods, for fixing bone with a bone plate supported temporarily at a slant on bone by a leg member before the bone plate is used as a lever to reposition a region of the bone. In some embodiments, the leg member may be a post member that attaches to the bone plate by threaded engagement with an aperture of the bone plate. In some embodiments, the bone plate and the leg member may be used near the end of a long bone, such as on a distal portion of a radial bone.

9 Claims, 4 Drawing Sheets

(51) Int. Cl.
*A61B 90/00* (2016.01)
*A61B 17/17* (2006.01)

(52) U.S. Cl.
CPC ... *A61B 2090/061* (2016.02); *A61B 2090/067* (2016.02)

(56) References Cited

U.S. PATENT DOCUMENTS

| | | | |
|---|---|---|---|
| 6,007,535 A | 12/1999 | Rayhack et al. | |
| 6,171,309 B1 | 1/2001 | Huebner | |
| 6,364,882 B1 | 4/2002 | Orbay | |
| 6,755,831 B2 | 6/2004 | Putnam et al. | |
| 7,250,053 B2 | 7/2007 | Orbay | |
| 7,282,053 B2 | 10/2007 | Orbay | |
| 7,635,381 B2 | 12/2009 | Orbay | |
| 2002/0143338 A1* | 10/2002 | Orbay | A61B 17/68 606/287 |
| 2003/0153918 A1 | 8/2003 | Putnam et al. | |
| 2004/0102778 A1* | 5/2004 | Huebner | A61B 17/1728 606/71 |
| 2004/0138662 A1* | 7/2004 | Landry | A61B 17/1604 606/86 A |
| 2004/0147928 A1* | 7/2004 | Landry | A61B 17/1671 606/86 A |
| 2006/0089648 A1* | 4/2006 | Masini | A61B 17/1615 606/71 |
| 2008/0097448 A1 | 4/2008 | Binder et al. | |
| 2008/0177322 A1* | 7/2008 | Davis | A61B 17/7038 606/266 |
| 2008/0230665 A1* | 9/2008 | Palermo | B60P 7/0815 248/231.71 |
| 2009/0227874 A1* | 9/2009 | Suri | A61B 8/4218 600/459 |
| 2009/0275947 A1 | 11/2009 | Graham et al. | |
| 2009/0281577 A1 | 11/2009 | Graham et al. | |
| 2009/0281578 A1* | 11/2009 | Spencer | A61B 17/02 606/280 |

OTHER PUBLICATIONS

Nelson, Dr. David L. et al., "Contour VPS Volar Plating System" Operative Technique brochure, Orthofix Inc., Jan. 2007, 16 pages.
Rüedi, Thomas P. et al., "Second Expanded Edition AO Principles of Fracture Management vol. 2—Specific Fractures", AO Publishing, pp. 659-661, undated.

* cited by examiner

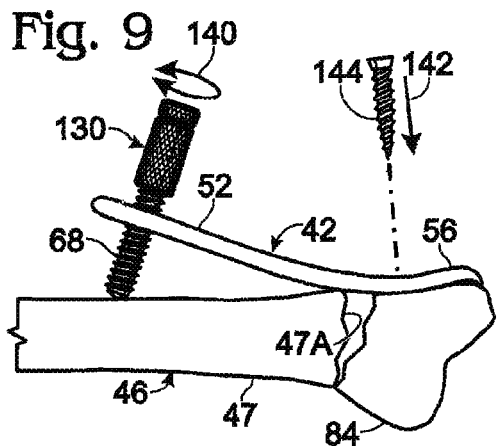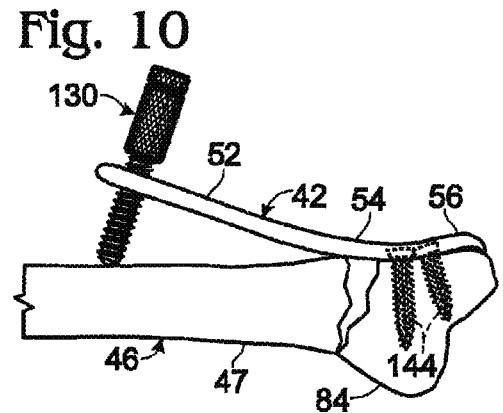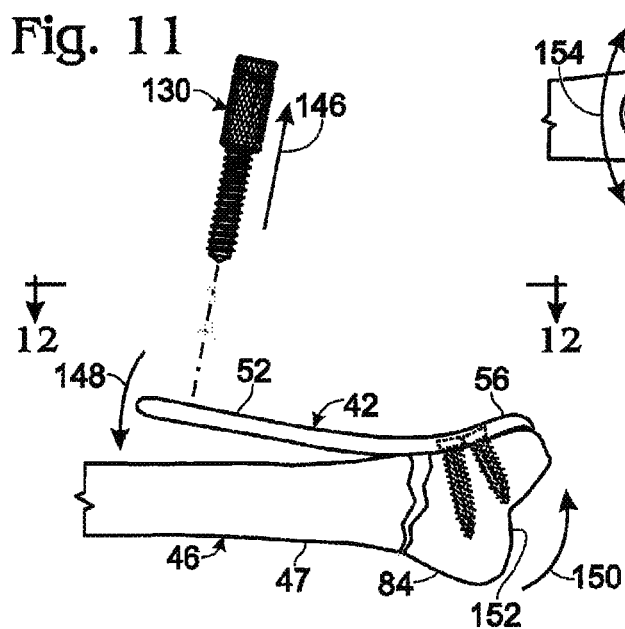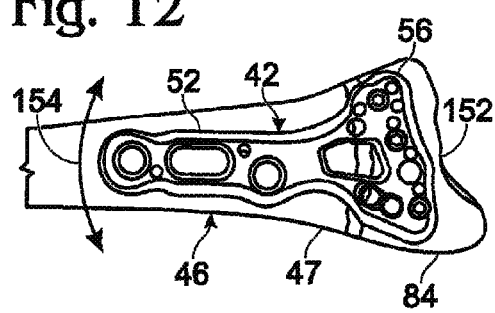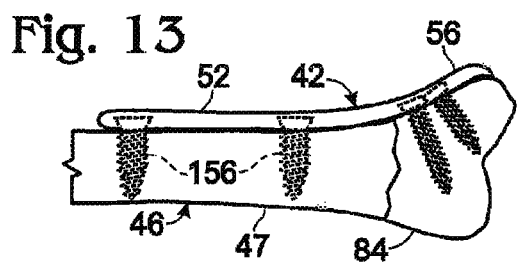

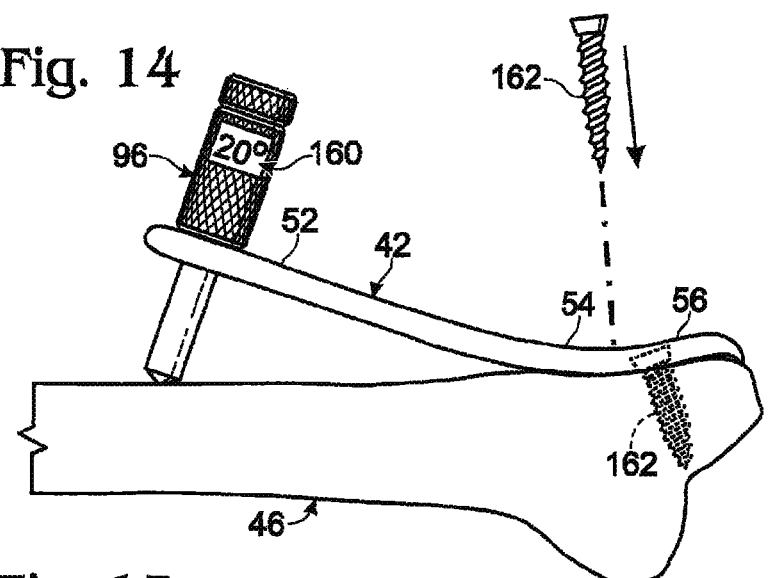
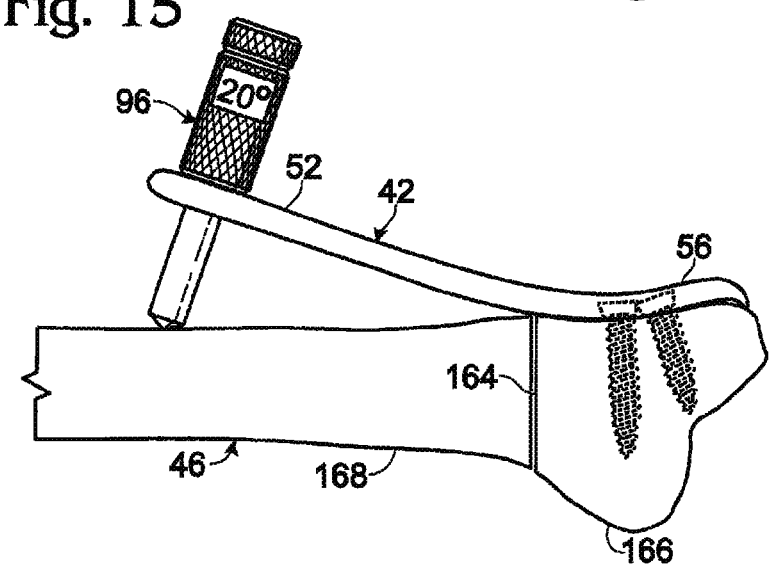
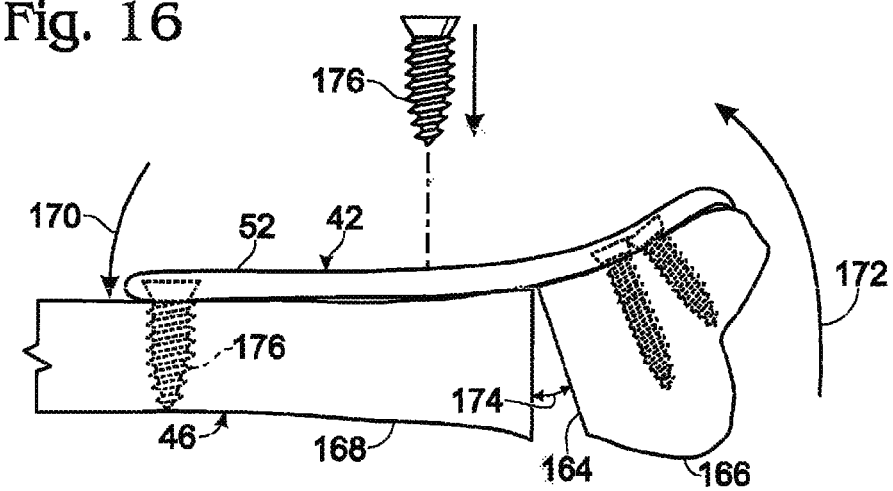

US 9,707,022 B2

BONE PLATE SUPPORTED BY A LEG MEMBER AND USED AS A LEVER

CROSS-REFERENCE TO PRIORITY APPLICATIONS

This application is a continuation of U.S. patent application Ser. No. 13/652,185, filed Oct. 15, 2012, now U.S. Pat. No. 9,414,871, which, in turn, is a continuation-in-part of U.S. patent application Ser. No. 13/246,684, filed Sep. 27, 2011, now U.S. Pat. No. 8,425,575, which, in turn, is based upon and claims the benefit under 35 U.S.C. §119(e) of U.S. Provisional Patent Application Ser. No. 61/386,925, filed Sep. 27, 2010. Each of these priority patent applications is incorporated herein by reference in its entirety for all purposes.

INTRODUCTION

The radius or radial bone is one of two long bones found in the human forearm. The radius, like other bones, is susceptible to a variety of fractures and deformities. For example, distal fractures of the radius are a common result, particularly among the elderly, of forward falls with the palms facing downward. In such falls, force exerted on the distal radius at impact can produce dorsal displacement and rotation of one or more bone fragments created distally to the fracture site.

Fixation of the fractured radius may be performed by internal fixation with a bone plate. The bone plate may be secured on the volar (or dorsal) surface of the distal radius with fasteners, such as bone screws or K-wires, among others. The bone plate may be pre-bent to follow the longitudinal profile of the volar (or dorsal) surface of the radius.

A fractured distal radius, if not fixed properly, may heal in a misshaped configuration, such as with an incorrect amount of volar tilt at the distal articular surface. This deformity can cause arthritis and the inability to rotate the wrist. To restructure the bone, a surgeon may perform a corrective osteotomy. A distal portion of a bone plate may be attached near the end of the radius, with a proximal portion of the bone plate forming a projecting arm extending at a slant above the shaft of the bone. The surgeon then may cut the bone at a position proximal to the site of attachment to create a distal bone fragment. The distal bone fragment may be pivoted into a more anatomically correct position by moving the projecting arm into contact with the shaft of the bone, followed by attachment of the arm to the shaft. However, a surgeon generally must guess an orientation for attachment of the bone plate, to slant the arm of the bone plate above the shaft of the bone at an angle that will provide a suitable angular correction. Also, the bone plate tends to slip or shift during attachment of the distal portion of the bone plate near the end of the bone, which alters the orientation of the bone plate's arm.

Better approaches are needed to use a projecting arm of a bone plate effectively to reposition a bone fragment.

SUMMARY

The present disclosure provides a system, including apparatus and methods, for fixing bone with a bone plate supported temporarily at a slant on bone by a leg member before the bone plate is used as a lever to reposition a region of the bone. In some embodiments, the leg member may be a post member that attaches to the bone plate by threaded engagement with an aperture of the bone plate. In some embodiments, the bone plate and the leg member may be used near the end of a long bone, such as on a distal portion of a radial bone.

BRIEF DESCRIPTION OF THE DRAWINGS

FIGS. 9-13 are somewhat schematic configurations produced during performance of an exemplary method of fixing a fractured bone using the bone plate of FIG. 1 and the leg member of FIG. 8, in accordance with aspects of the present disclosure.

FIGS. 14-16 are somewhat schematic configurations produced during performance of an exemplary method of fixing a cut bone using the bone plate and leg member of FIG. 1, in accordance with aspects of the present disclosure.

DETAILED DESCRIPTION

Figure 1:
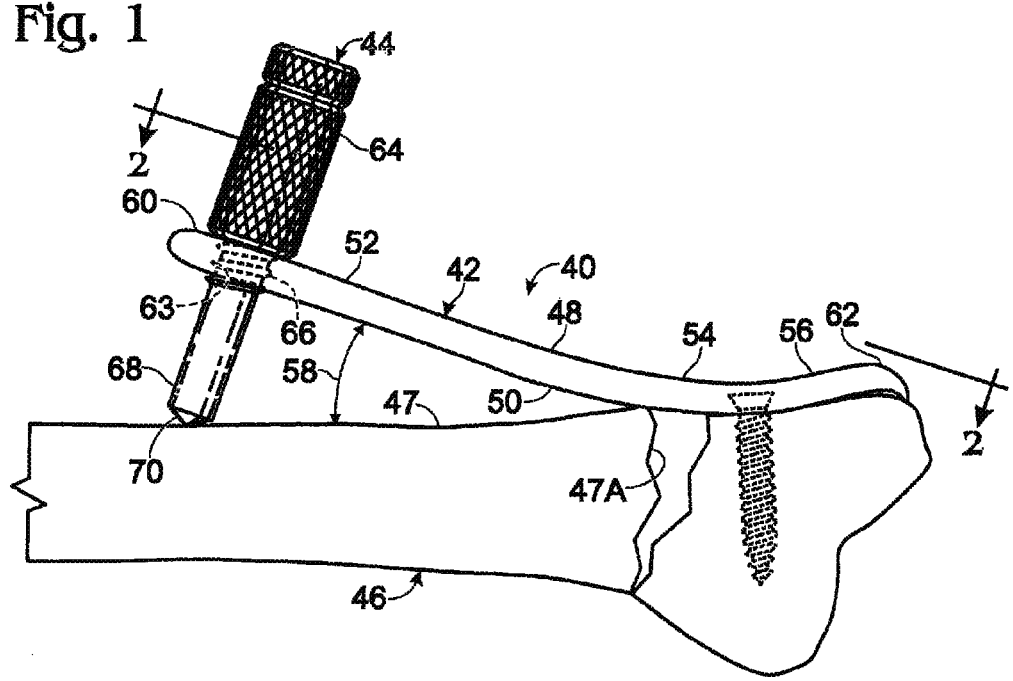
FIG. 1 is a side view of selected aspects of an exemplary embodiment of a bone fixation system including a bone plate and a detachable leg member temporarily supporting an arm portion of the bone plate at a slant above a shaft of a fractured radial bone, in accordance with aspects of the present disclosure.

The present disclosure provides a system, including apparatus and methods, for fixing bone with a bone plate supported temporarily at a slant on bone by a leg member before the bone plate is used as a lever to reposition a region of the bone. In some embodiments, the leg member may be a post member that attaches to the bone plate by threaded engagement with an aperture of the bone plate. In some embodiments, the bone plate and the leg member may be used near the end of a long bone, such as on a distal portion of a radial bone.

An exemplary method of bone fixation is provided. In the method, a bone plate including a first portion and a second portion may be selected. A leg member may be disposed on the bone with the leg member attached to and projecting from the first portion of the bone plate to a first region of the bone, such that the first portion of the bone plate is supported at a slant with respect to the first region and spaced from the bone. The second portion of the bone plate may be attached to a second region of the bone. The leg member may be disconnected from the bone plate. The first portion of the bone plate may be pivoted toward the first region of the bone such that the bone plate is used as a lever to change an orientation of the second region relative to the first region of the bone. The first portion of the bone plate may be attached to the first region of the bone.

Another exemplary method of bone fixation is provided. In the method, a bone plate may be selected. The bone plate may include an elongated body portion connected to a head portion that is wider than the body portion. A leg member may be disposed on the bone with the leg member attached to and projecting from the body portion of the bone plate to a shaft region of the bone, such that the body portion of the bone plate is supported at a slant above the shaft region. The head portion of the bone plate may be attached to an end region of the bone. The leg member may be disconnected from the bone plate. The body portion of the bone plate may be pivoted toward the shaft region of the bone such that the bone plate is used as a lever to change an orientation of the end region relative to the shaft region of the bone. The body portion of the bone plate may be attached to the shaft region of the bone.

Yet another exemplary method of bone fixation is provided. In the method, a bone plate may be selected. The bone plate may include an arm portion, a fulcrum portion, and an anchor portion arranged in order along the bone plate. A post member may be disposed on the bone with the post member extending through an aperture of the arm portion to a first region of bone and attached to the arm portion at the aperture, such that the fulcrum portion and the post member collectively support the arm portion in a spaced relation to the bone and at a slant with respect to the first region of the bone. The anchor portion of the bone plate may be attached to a second region of the bone. The leg member may be disconnected from the bone plate. The arm portion of the bone plate may be pivoted toward the first region of the bone such that the bone plate is used as a lever to change an orientation of the second region relative to the first region of the bone. The arm portion of the bone plate may be attached to the first region of the bone.

An exemplary system for bone fixation is provided. The system may comprise a bone plate including an arm portion and an anchor portion separated from the arm portion by a fulcrum portion. Each of the arm portion and the anchor portion may define one or more apertures for receiving fasteners that attach the bone plate to bone. The system also may comprise a thumbscrew including a graspable handle portion affixed to a shaft portion having an external thread. The shaft portion may be configured to be disposed in threaded engagement with an aperture of the arm portion, such that the handle portion projects from an outer surface of the arm portion, and such that the shaft portion projects from an inner surface of the arm portion, to enable support of the arm portion at a slant above a bone surface by the thumbscrew and the fulcrum portion of the bone plate.

The system disclosed herein has substantial advantages over bone fixation systems lacking a leg member. For example, the leg member may reduce undesired plate movement while another portion of the bone plate is being attached to an end region of bone, permitting a surgeon to more accurately direct fasteners into bone, with less plate slippage. Also, the leg member may enable a surgeon to support an arm portion of a bone plate at a desired and/or predefined angle above a shaft region of a bone, to introduce a corresponding change in angular disposition of the end region of a bone when the arm portion is moved into alignment with the shaft region. Thus, the system may enable more accurate angular repositioning of bone fragments in corrective osteotomy or during reduction of a fractured bone.

Further aspects of the present disclosure are described in the following sections: (I) overview of an exemplary bone fixation system with a leg member, (II) exemplary method of fixing a fractured bone, (III) exemplary method of bone fixation with corrective osteotomy, (IV) bone plates, (V) leg members, and (VI) selected embodiments.

I. Overview of an Exemplary Bone Fixation System with a Leg Member

FIG. 1 shows selected aspects of an exemplary bone fixation system 40 including a bone plate 42 connected to a detachable leg member 44 that provisionally supports a portion of the bone plate in a spaced relation to a bone 46, particularly a shaft region (and/or a shaft fragment) 47 of the bone. Here, bone 46 is a radial bone that has sustained a fracture 47A, and fixation system 40 is disposed on a distal volar surface region of the radial bone.

The bone plate has opposing outer and inner surfaces 48, 50 configured to face, respectively, away from and toward bone 46. The plate bone is depicted here in profile, which reveals an upward longitudinal bend. However, in other embodiments, the bone plate may have a substantially linear profile or a downward longitudinal bend, among others.

The bone plate may include an arm portion 52 (interchangeably termed a lever portion), an intermediate or fulcrum portion 54, and an anchor portion 56 arranged in order along the bone plate. The arm portion may be supported in a spaced relation to bone by a set of contacts provided collectively by leg member 44 and fulcrum portion 54 and/or anchor portion 56. For example, fulcrum portion 54 (or anchor portion 56), due to its width, may provide at least two points of contact with bone 46, and leg member 44 may provide at least one more point of contact with the bone. In any event, leg member 44 may support arm portion 52 at a slant, in a spaced configuration from an adjacent surface area of bone 46 (and shaft region 47), such that the bone plate and the bone diverge as arm portion 52 extends away from fulcrum portion 54. Accordingly, an acute angle 58 may be formed between arm portion 52 and shaft region 47 and/or may be defined collectively by arm portion 52 and bone 46.

Leg member 44 may be attached to the arm portion of the bone plate, such that at least part of the leg member projects below the bone plate, in a direction transverse (e.g., substantially orthogonally) to the arm portion. For example, the leg member may project from inner surface 50 (and, optionally, outer surface 48) of the bone plate. The leg member may be attached by any suitable mechanism that allows subsequent detachment, such as threaded engagement with the arm portion, one or more clips, a sleeve, a mated snap-fit, etc. The leg member may be attached to the bone plate near one of the plate's opposing ends 60, 62, such as the proximal end in the depicted embodiment. The leg member, when attached to the bone plate, may extend through an aperture 63 of the bone plate. The leg member may provide an upper portion 64 projecting above outer surface 48 of the bone plate, an intermediate portion 66 locked to the bone plate in aperture 63, and a lower or spacer portion 68 that projects below inner surface 50 of the bone plate. Spacer portion 68 may extend to a distal tip 70, such as a pointed or blunt tip, that contacts bone. The length of spacer portion 68 and its distance of separation from fulcrum portion 54 (and/or anchor portion 56) of the bone plate generally determine the magnitude of acute angle 58 at which arm portion 52 is supported relative to shaft region 47 and how far an end (e.g., proximal end 60) of the bone plate is spaced from bone 46.

Figure 2:
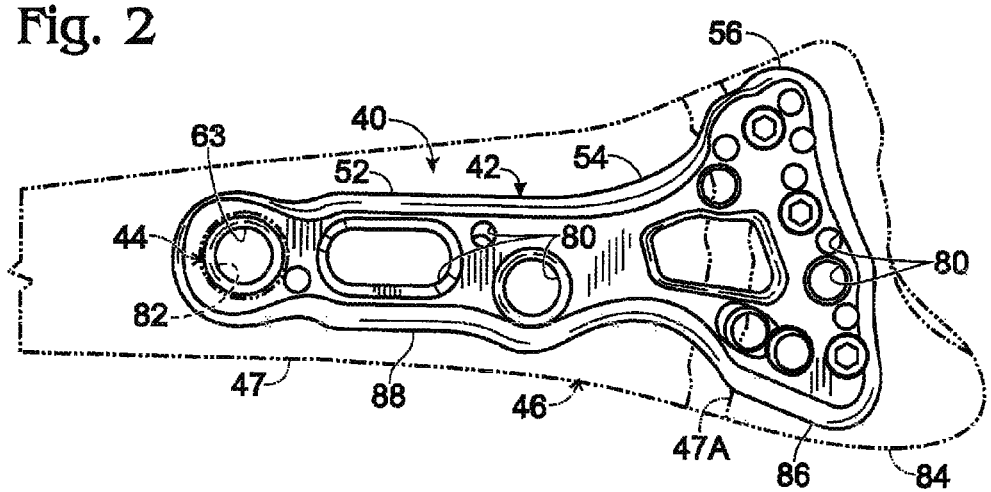
FIG. 2 is a top view of the bone plate and bone of FIG. 1 taken generally along line 2-2 of FIG. 1 with the leg member removed.
Figure 3:
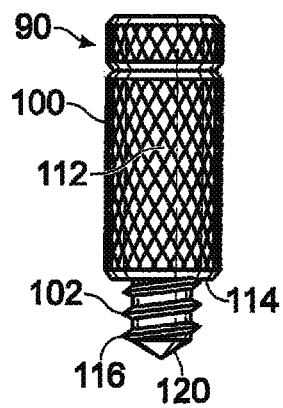
FIGS. 3-7 are side views of exemplary leg members, structured as post members, for use in the system of FIG. 1, with the leg members designed to support an arm portion of the bone plate at a predefined angle of about 5°, 10°, 15°, 20°, and 25°, respectively, above a shaft surface region of bone, in accordance with aspects of the present disclosure.
Figure 4:
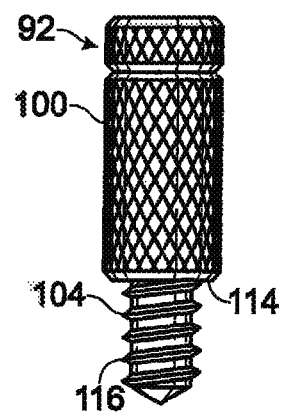
Figure 5:
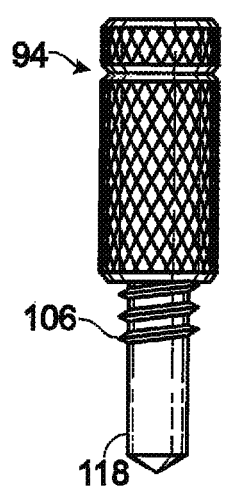

FIG. 2 shows a top view of bone plate 42, including arm portion 52, fulcrum portion 54, and anchor portion 56, and with leg member 44 removed. (The perimeter of leg member 44 is shown in phantom outline.) Each of the arm portion and the anchor portion may define a plurality of apertures 80 (e.g., through-holes) to receive fasteners (e.g., bone screws, wires, a screw to attach a target guide or handle, etc.). Each of the apertures may be locking (e.g., having an internal thread) or nonlocking (e.g., lacking an internal thread). At least one aperture in arm portion 52, such as aperture 63, may include a locking structure, such as an internal thread 82, adapted to provide locked engagement with an external thread of the leg member.

Bone plate 42 may be used to fix an end region 84 of bone 46 relative to shaft region 47. The bone plate may include a relatively wider head portion 86 connected to a relatively narrower body portion 88, which may be elongated. Head portion 86 may be disposed closer to the end of the bone than body portion 88, such as distally on the radial bone, and corresponds to anchor portion 56. The body portion may be disposed more centrally along the bone, such as more proximally on the radial bone, and corresponds to arm portion 52. Fulcrum portion 54 of the bone plate may be disposed generally between head portion 86 and body portion 88.

FIGS. 3-7 show exemplary leg members 90-98 for use in fixation system 40 with bone plate 42. Each leg member 90-98 is designed to support the arm portion of the bone plate at a predefined angle of about 5°, 10°, 15°, 20°, and 25°, respectively, with respect to an adjacent surface region of bone. Each leg member may be marked with one or more indicia, such as with one or more alphanumeric characters (e.g., a number, such as "15"), to identify the angle at which the leg member is configured to support the arm portion.

Each leg member 90-98 may be structured as a post member. The post member may include a graspable handle or head portion 100 connected to a respective shaft portion 102-110, which may be of smaller width/diameter than the handle/head portion. The handle portion may include a knurled surface 112 with ridges formed on sides of the handle to facilitate manual engagement (e.g., with a gloved (or ungloved) hand of a surgeon). The post member (e.g., the head and/or shaft portion) may form a stop structure 114 (e.g., a shoulder) that blocks axial advancement of the post member through an aperture of the bone plate. In other words, the stop structure may form an abutment with the bone plate that determines a fully advanced position of the post member. In some embodiments, the post member may be described as a thumbscrew, which may be any screw configured to be turned by hand via an integral, graspable head.

Each shaft portion of the post member may include an external thread 116, which may extend along any suitable portion, a majority, or at least substantially all of the length of the shaft portion. The shaft portion may (or may not) include a nonthreaded region 118 (e.g., see FIGS. 5-7) and may extend to a distal tip 120 (see FIG. 3). The distance of tip 120 from stop structure 114 is different for each post member of FIGS. 3-8. This distance determines how much of the post member, and particularly the shaft portion thereof, projects below the bone plate when stop structure 114 is abutted with the bone plate, and thus the angle at which the arm portion of the bone plate is supported relative to bone.

Figure 7:
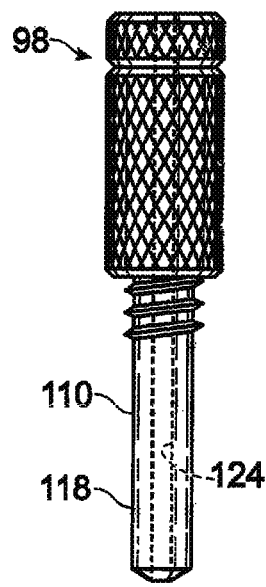

The post member may have a through-bore 124 extending lengthwise through the post member (see FIG. 7). The through-bore, which may be described as a cannulation, may be utilized to receive a wire (such as a K-wire) that extends through the post member and, optionally, into bone. The wire may help to hold the post member in place on the bone, may be used to guide the post member on the bone, and/or may be visualized under fluoroscopy to project the axis defined by the post member into bone, among others.

Figure 8:
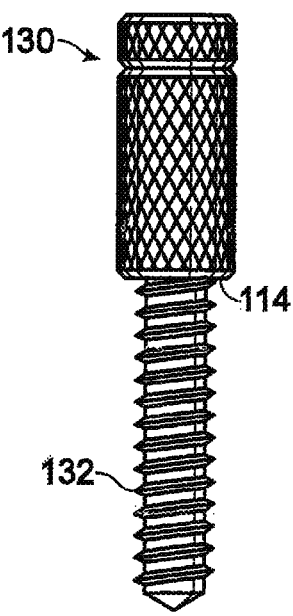
FIG. 8 is a side view of another exemplary leg member structured as a post member for use in the system of FIG. 1, with the leg member designed to support an arm portion of the bone plate at a continuous range of angles from about 0° to 30° above a shaft surface region of bone, in accordance with aspects of the present disclosure.

FIG. 8 shows another exemplary leg member 130 structured as a post member for use in system 40 with bone plate 42 (see FIG. 1). Leg member 130 may be designed to support the arm portion of the bone plate at a continuous range of angles from about 0° to 30°, based on how far a threaded shaft 132 of the leg member is advanced through the bone plate. If leg member 130 is advanced fully, such that stop structure 114 engages the bone plate, the leg member may support the arm portion of the bone plate at about 30°.

The bone fixation system may be provided as a kit. The kit may include at least one bone plate, one or more leg members, fasteners (e.g., bone screws) to attach the bone plate to bone, a protractor, a saw for cutting bone, a guide device to guide a drill bit and/or fasteners through apertures of the bone plate and into bone, and/or the like. In some embodiments, the kit may include a bone plate and a set of two or more leg members that assemble interchangeably with the bone plate to support an arm portion of the bone plate at two or more predefined angles, such as two or more predefined angles that differ from each other by an increment of about 1, 2, 3, 4, or 5 degrees, or an integer multiple thereof, among others. The two or more leg members may be post members with shafts of different length. The components of a kit may be supplied in a sterile package. Some of the components may be configured to be re-used (e.g., the protractor, saw, and guide device) and others may be configured to be used only once (e.g., the bone plate and fasteners).

The bone plate and leg members disclosed herein may be formed of any suitable biocompatible material(s). Exemplary biocompatible materials include (1) metals (for example, titanium or titanium alloys, alloys with cobalt and chromium (cobalt-chrome), stainless steel, etc.); (2) plastics/polymers (for example, ultra-high molecular weight polyethylene (UHMWPE), polymethylmethacrylate (PMMA), polytetrafluoroethylene (PTFE), polyetheretherketone (PEEK), nylon, polypropylene, and/or PMMA/polyhydroxyethylmethacrylate (PHEMA)); (3) ceramics (for example, alumina, beryllia, and/or zirconia, among others); (4) composites (e.g., a polymer matrix (such as PEEK) containing carbon fibers and/or ceramic); (5) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, other bioresorbable polyesters, etc.; and/or the like. In exemplary embodiments, both the bone plate and the leg members are formed of metal. For example, the bone plate may be formed of titanium (such as a titanium alloy) and the leg member of surgical grade stainless steel.

II. Exemplary Method of Fixing a Fractured Bone

FIGS. 9-13 show somewhat schematic configurations produced during performance of an exemplary method of fixing fractured bone 46 using bone plate 42 and leg member 130 (see FIGS. 1 and 8). The method may include any suitable combination of the steps disclosed in this section or elsewhere in the present disclosure, performed in any suitable order. In some embodiments, the method may reduce and fix a bone, such as a radial bone fractured distally.

A bone may be selected for fixation. The bone may have any suitable discontinuity or may be a candidate for an osteotomy. Exemplary bones that may be selected are long bones, such as a femur, tibia, fibula, ulna, radius, humerus, or the like. In some embodiments, the bone may include an end region that has an undesired angular disposition relative to a shaft region of the bone. The undesired angular disposition may be the result of displacement caused by fracture, a malunion, a growth deformity, or the like.

A bone plate and a leg member may be selected. The leg member may be continuously adjustable (e.g., leg member 130 of FIG. 8) and/or may provide a predefined angle of support. The leg member may be selected from a set of two or more leg members that provide different predefined angles of support and/or have spacer portions 68 (and/or shafts) of different length (see FIGS. 1 and 3-8). In some cases, a continuously adjustable leg member may be more suitable for fracture fixation.

Bone plate 42 and leg member 130 may be disposed on the bone such that the leg member is attached to the bone plate and spaces arm portion 52 from the bone. The leg member may be attached to the bone plate before or after the bone plate is disposed on the bone. Accordingly, the bone plate and leg member may be assembled with each other off bone (e.g., by a manufacturer or peri-operatively) or on bone. The bone plate may be positioned to span a discontinuity in the bone (such as fracture 47A) and/or a prospective osteotomy site.

FIG. 9 shows bone plate 42 and leg member 130 assembled with each other and disposed on fractured bone 46. The leg member, which may be described as a jackscrew, is locked to the bone plate. The leg member may support arm portion 52 of the bone plate at a predefined slant relative to shaft region 47 of bone 46.

End region 84 of the bone has been displaced at least in part by rotation out of alignment with shaft region 47 as a consequence of fracture 47A. The bone plate may have an inner surface region (e.g., provided by anchor portion 56) that is contoured to be complementary to an end surface region of bone 46 (e.g., on end region 84). The inner surface region of the bone plate thus may serve as a template for reconstruction of the bone. Accordingly, in some embodiments, leg member 130 may be turned at this stage of the procedure, indicated at 140, to change the acute angle formed between shaft region 47 and arm portion 52, to adjust the fit of the inner surface region of anchor portion 56 on end region 84. In other words, arm portion 52 may be raised or lowered, to pivot anchor portion 56 in order to improve the abutment of anchor portion 56 and end region 84, at least in part by matching the angular disposition of end region 84 with that of anchor portion 56. Adjustment of the length of spacer portion 68 of leg member 130 that projects below the bone plate, while the leg member is supporting arm portion 52, may produce coincident pivotal motion of arm portion 52 and anchor portion 56.

FIG. 10 shows an attached configuration of bone plate 42. Anchor portion 56 may be attached to end region 84 of the bone while arm portion 52 is supported by leg member 130 and fulcrum portion 54. Attachment may include placement of fasteners, indicated at 142 in FIG. 9, such as one or more bone screws 144, through one or more apertures of the anchor portion and into end region 84 of the bone. During this procedure, the leg member may stabilize the position of the bone plate by restricting pivotal and translational motion thereof. In some embodiments, anchor portion 56 may be attached to end region 84 before leg member 130 engages shaft region 47 of bone 46.

FIG. 11 shows an adjustable configuration of the fractured bone in which bone plate 42 is poised to function as a lever. Leg member 130 may be manipulated, indicated at 146, to remove the support previously provided to the bone plate by the leg member. For example, in the present illustration, the leg member has been disconnected from the bone plate and removed by unthreading the leg member from arm portion 52. As a result, arm portion 52 can be urged toward shaft region 47 by pivoting the arm portion, indicated by a motion arrow at 148. A fulcrum for pivotal movement may be formed by contact of the fulcrum portion of the bone plate with shaft region 47 near the fracture, with adjacent soft tissue, and/or with one or more intermediate bone fragments, among others.

Motion of the arm portion adjusts an orientation of end region 84, as indicated by a motion arrow at 150. The motion may set the palmar inclination (also called the palmar tilt) of a distal articular surface 152 of the radial bone. (The term "palmar" may be used as a synonym for "volar.") The palmar inclination is defined as the angle between a first line drawn perpendicular to the long axis of the radius and a second line drawn between the dorsal and palmar lips of the distal radial articular surface. An exemplary palmar inclination is about 12 degrees (with the dorsal lip disposed more distally than the palmar lip).

FIG. 12 shows a volar view of bone 46 with plate 42 attached to end region 84, taken generally along line 12-12 of FIG. 11. Arm portion 52 also may be moved pivotally, indicated by a motion arrow at 154, to set a radial inclination of distal articular surface 152 of bone 46. The radial inclination is defined as the angle between a first line drawn perpendicular to the long axis of the radius at the outer corner of the lunate fossa of surface 152 and a second line drawn between the outer corner of the lunate fossa and the tip of the radial styloid. An exemplary radial inclination is about 23 degrees.

FIG. 13 shows arm portion 52 attached to shaft region 47 to stabilize the adjusted orientation of end region 84. The arm portion has been pivoted into alignment with shaft region 47, such that the arm portion is no longer spaced and slanted with respect to the shaft region. End region 84 has been pivoted by a corresponding amount to an adjusted orientation that reduces the fractured bone by improving the alignment of the shaft and end regions of the bone. Attachment may include placement of fasteners, such as one or more bone screws 156, through one or more apertures of the arm portion and into the shaft region of the bone.

III. Exemplary Method of Bone Fixation with Corrective Osteotomy

Figure 6:
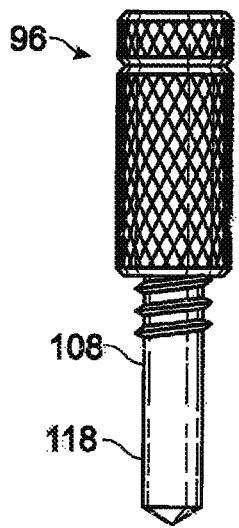

FIGS. 14-16 show somewhat schematic configurations produced during performance of an exemplary method of fixing a cut bone using bone plate 42 (FIGS. 1 and 2) and leg member 96 (FIG. 6). The method may include any combination of the steps disclosed in this section or elsewhere in the present disclosure, performed in any suitable order. In some embodiments, the method may be performed as part of a corrective osteotomy. In an osteotomy, a bone is cut and then realigned, shortened, or lengthened to correct a defect. The method may be performed on any of the bones listed above in the preceding section. In the present illustration, radial bone 46 is cut, realigned, and fixed.

A surgeon may estimate the amount of angular correction needed, and choose the appropriate leg member from a set of leg members offering different angular corrections. In this example, leg member 96 is selected to provide a 20-degree correction. The leg member may be marked with indicia 160 to facilitate identification of the leg member.

FIG. 14 shows bone plate 42 supported by leg member 96 proximally and being attached distally on the volar surface of radius 46 distally with bone screws 162. Bone plate 42 may be supported distally, prior to attachment with bone screws 162, by contact of radius 160 with fulcrum portion 54 and/or anchor portion 56 of the bone plate.

FIG. 15 shows a cut 164 placed through radius 46 proximal to secured anchor portion 56 of the bone plate. The cut may be formed with a saw and may create a distal bone fragment (an end fragment) 166 and a main, proximal bone fragment (a shaft fragment) 168.

FIG. 16 shows bone plate 42 and radius 46 after removal of leg member 96 and pivotal movement, indicated at 170 of arm portion 52 of the bone plate into alignment with shaft fragment 168. Pivotal movement of arm portion 52 may also produce a corresponding pivotal movement of end fragment 166, indicated at 172. The leg member is designed to support arm portion 52 at an angle of 20 degrees with respect to a shaft surface region of radius 46. Accordingly, pivoting arm portion 52 through an angle of 20 degrees, to place the arm portion against proximal bone fragment 168, causes a corresponding rotation of 20 degrees of distal bone fragment 166, which may create a 20-degree gap 170. The arm portion then may be secured to proximal fragment 168 of the radius with fasteners, such as bone screws 176, to fix the bone. The 20-degree gap may be filled, for example, via natural healing and/or a bone graft, so that the bone ends up with the desired shape.

IV. Bone Plates

A bone plate generally refers to any structure or piece having a plate geometry and being configured to be attached to bone with the bone plate at least mostly or completely under skin (and, generally, other soft tissue). The bone plate may be configured to reduce irritation to the bone and surrounding soft tissue. For example, the bone plate may have a low and/or feathered profile to reduce its protrusion into overlying soft tissue and rounded, burr-free surfaces to reduce the effects of such protrusion.

The bone plates of the present disclosure may have any shape suitable for use on their intended target bones. The bone plate may be shaped for use on any suitable bone or bones to be fixed, including a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a clavicle, a rib, a scapula, a pelvic bone, a vertebra, a skull, a mandible, or the like.

Each bone plate may be configured for use on any suitable side or sides of the body. For example, the bone plate may be configured for use on both the left side and right side of the body/skeleton, such as when the bone plate is bilaterally symmetrical. Alternatively, each bone plate may be configured for use on either the left side or right side of the body/skeleton, but not both.

Each bone plate may have any suitable contour. In some examples, the bone plate may be supplied in a pre-contoured configuration produced during plate manufacture (e.g., by bending, molding, and/or machining, among others) to include an inner surface region that is complementary to a nonplanar surface region of a target bone. The bone plate thus may be pre-contoured according to an average or representative surface geometry of a target bone. Alternatively, or in addition, the bone plate may be contoured peri-operatively (e.g., by bending the bone plate), to adjust its shape before and/or during its installation on bone, to improve, for example, the fit of the bone plate on a target bone for particular individuals and/or on distinct regions of the target bone.

Each bone plate may be generally elongate, with length L>width W>thickness T. In use, the long axis of the bone plate may be aligned with the long axis of a target bone and/or may extend obliquely and/or transversely relative to the long axis. In some embodiments, the bone plate may have a length and a width that are about the same.

Each bone plate may be of continuous structure (e.g., monolithic) or may include two or more discrete pieces. The two or more discrete pieces may be fixed to one another or may be connected through a mechanical joint that enables translational and/or pivotal movement to adjust the shape and/or size of the bone plate.

The bone plate may include a first portion and a second portion, which may be arranged along the bone plate from each other. Each of the first portion and the second portion may be anchor portion (i.e., an attachment portion) defining one or more apertures for receiving fasteners that secure the anchor portion to bone. At least one of the anchor portions also may be described as an arm portion, a head portion, and/or a body portion, among others. An arm portion is any part of a bone plate that is supportable in a spaced relation to bone and then can be pivoted toward the bone.

V. Leg Members

The bone fixation systems disclosed herein utilize a leg member to temporarily support part of a bone plate in a spaced relation to bone, such as at a slant above a shaft region of a bone. A leg member generally comprises any detachable support that can prop up an end region of a bone plate while the opposing end region is being attached to bone. A leg member projects below an inner surface of the bone plate by any suitable distance. The leg member may project orthogonally or obliquely from the inner surface. In some cases, the leg member or a portion thereof may be described as a jackscrew, a stand, a bolt, a post, a kickstand, or a combination thereof.

The leg member may have any suitable shape. The leg member may be elongate. The leg member or regions thereof may or may not be at least generally cylindrical. For example, the leg member may include a cylindrical head/handle portion, a cylindrical shaft portion that extends through the bone plate and/or projects below the bone plate, or a combination thereof, among others.

Any suitable connection may be formed between the leg member and a bone plate. The leg member may be locked to the bone plate, such that axial motion of the leg member is restricted in both axial directions of the leg member. Alternatively, the leg member may support part of the bone plate without locked engagement. For example, the leg member may provide a post with a flange on which the bone plate rests, such that the flange restricts separation of the leg member from the bone plate in only one of two axial directions of the leg member. In other embodiments, the leg member may slide onto the bone plate from an end thereof, may clip onto the bone plate, or the like.

VI. Selected Embodiments

This section describes selected embodiments of the present disclosure, presented as a series of indexed paragraphs.

These embodiments are intended for illustration and should not limit the entire scope of the present disclosure.

1. A method of bone fixation, comprising: (A) supporting an arm portion of a bone plate in a spaced relation to a shaft region of a bone with a leg member connected to the arm portion and engaged with the shaft region; (B) attaching an anchor portion of the bone plate to an end region of the bone; (C) manipulating the leg member to remove the leg member's support of the arm portion; (D) moving the arm portion toward the shaft region of the bone to adjust an orientation of the end region of the bone; and (E) attaching the arm portion to the shaft region to stabilize the adjusted orientation.

2. The method of paragraph 1, further comprising a step of disposing the leg member in threaded engagement with the arm portion.

3. The method of paragraph 2, wherein the leg member includes a handle portion, and wherein the step of disposing the leg member in threaded engagement includes a step of turning the handle portion with the handle portion grasped manually.

4. The method of paragraph 1, wherein the step of supporting includes a step of supporting the arm portion with the leg member at a predefined angle with respect to the shaft region.

5. The method of paragraph 4, further comprising a step of selecting the leg member from a set of two or more leg members providing different predefined angles of support for the arm portion.

6. The method of paragraph 4, wherein the leg member has a position where advancement through an aperture of the bone plate is stopped, and wherein the position provides the predefined angle.

7. The method of paragraph 6, wherein the leg member includes a head and a shaft, and wherein the position is achieved when the head engages the arm portion.

8. The method of paragraph 1, wherein the step of supporting includes a step of supporting the arm portion at a slant with respect to the shaft region, and wherein the leg member is configured to be adjustable to provide a continuous range of angles for the slant.

9. The method of paragraph 8, further comprising a step of adjusting the slant to provide a better fit of the anchor portion on the end region of the bone.

10. The method of paragraph 1, further comprising a step of cutting the bone to separate the shaft region from the end region before the step of moving.

11. The method of paragraph 1, wherein the shaft region and the end region of the bone are separated by a fracture in the bone.

12. The method of paragraph 1, wherein the step of manipulating includes a step of unthreading the leg member from the arm portion.

13. The method of paragraph 1, wherein the step of moving includes a step of pivoting the arm portion of the bone plate.

14. A system for bone fixation, comprising: (A) a bone plate including an anchor portion and an arm portion each defining one or more apertures; and (B) a leg member including a graspable handle portion connected to a shaft portion, the shaft portion being configured to be disposed in threaded engagement with an aperture of the arm portion of the bone plate, with the handle portion projecting above the bone plate, such that part of the shaft portion extends below the bone plate to permit support of the arm portion of the bone plate in a spaced relation to a shaft region of a bone.

15. A system for bone fixation, comprising: (A) a bone plate including an anchor portion and an arm portion each defining one or more apertures and also including a fulcrum; and (B) a post member including a handle portion connected to a shaft portion, the shaft portion being configured to be disposed in threaded engagement with an aperture of the arm portion of the bone plate such that part of the shaft portion extends below the bone plate to provide support of the arm portion of the bone plate at a predefined angle and such that the handle portion projects above the bone plate.

16. A system for bone fixation, comprising: (A) a bone plate including an anchor portion and an arm portion each defining one or more apertures; and (B) at least two posts each including a head portion connected to a shaft portion, each shaft portion being configured to be disposed in threaded engagement with an aperture of the arm portion of the bone plate such that part of the shaft portion extends below the bone plate to provide support of the arm portion of the bone plate at a predefined angle, wherein the leg members are configured to provide different predefined angles of support.

17. A method of fixing bone, comprising: (A) selecting a bone plate including a first portion and a second portion; (B) disposing the bone plate and a discrete leg member on the bone such that the leg member is attached to and projects from the first portion of the bone plate to a first region of the bone, to position the first portion of the bone plate at a slant with respect to the first region and spaced from the bone; (C) attaching the second portion of the bone plate to a second region of the bone; (D) pivoting the first portion of the bone plate toward the first region of the bone such that the bone plate is used as a lever to change an orientation of the second region relative to the first region of the bone; and (E) attaching the first portion of the bone plate to the first region of the bone.

18. The method of paragraph 17, wherein the step of disposing positions the first portion at a predefined angle with respect to the first region of the bone.

19. The method of paragraph 18, wherein the leg member has a stop structure that blocks advancement through an aperture of the first portion of the bone plate at a position of the leg member.

20. The method of paragraph 19, wherein stop structure is a shoulder formed by the leg member.

21. The method of paragraph 17, further comprising a step of selecting the leg member from a set of two or more leg members each extending a different predefined distance from the first portion when attached to the bone plate.

22. The method of paragraph 17, wherein the leg member is configured to be adjustably advanced with respect to the arm portion to provide a continuous range of angles for the slant of the first portion of the bone plate.

23. The method of paragraph 17, wherein the first region is a shaft region and the second region is an end region of the bone, 24. The method of paragraph 23, further comprising a step of cutting the bone to separate the shaft region from the end region before the step of pivoting.

25. The method of paragraph 23, wherein the shaft region and the end region of the bone are separated by a fracture in the bone.

26. A system for bone fixation, comprising: (A) a bone plate including an arm portion and an anchor portion separated from the arm portion by a fulcrum portion, each of the arm portion and the anchor portion defining one or more apertures for receiving fasteners that attach the bone plate to bone; and (B) a thumbscrew including a graspable handle portion affixed to a shaft portion having an external thread, the shaft portion being configured to be disposed in threaded engagement with an aperture of the arm portion, such that the handle portion projects from an outer surface of the arm portion, and such that the shaft portion projects from an inner surface of the arm portion, to enable support of the arm portion at a slant above a bone surface by the thumbscrew and the fulcrum portion of the bone plate before use of the bone plate as a lever.

27. The system of paragraph 26, wherein the thumbscrew is in threaded engagement with the aperture and restricted from further advancement into the aperture, and wherein a projecting region of the shaft portion projects into air from the inner surface of the arm portion to a distal tip of the shaft portion.

28. The system of paragraph 26, wherein the graspable handle portion of the thumbscrew is substantially permanently affixed to the shaft portion.

29. The system of paragraph 26, wherein the graspable handle portion is cylindrical.

30. The system of paragraph 26, wherein the graspable handle portion includes a knurled surface region.

31. The system of paragraph 26, wherein the thumbscrew defines a long axis, and wherein the graspable handle portion is elongated in a direction parallel to the long axis.

32. The system of paragraph 26, wherein the thumbscrew is a first thumbscrew, further comprising a second thumbscrew configured to be disposed in threaded engagement with the aperture of the arm portion of the bone plate, and wherein each of the first and second thumbscrews is configured to support the arm portion at a respective different predefined angle of slant when fully advanced into the aperture.

33. The system of paragraph 32, wherein the predefined angle of slant for the first thumbscrew and the second thumbscrew differ from each other by about five or ten degrees.

34. The system of paragraph 32, wherein each of the first and second thumbscrews is marked with at least one indicium identifying an angle of slant at which the thumbscrew supports the arm portion.

35. The system of paragraph 26, wherein the anchor portion is wider than the arm portion.

36. The system of paragraph 26, wherein the anchor portion has an inner surface that is contoured to match a surface region near an end of a bone, such that the anchor portion fits onto the surface region.

37. The system of paragraph 36, wherein the anchor portion has an inner surface that is contoured to match a surface region near a distal end of a radial bone.

38. The system of paragraph 37, wherein the bone plate has a longitudinal bend that renders an outer surface of the bone plate at least substantially concave in profile.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A system for bone fixation, comprising:
a monolithic bone plate including an arm portion and an anchor portion separated from one another by a fulcrum portion, the anchor portion being wider than the arm portion, each of the arm portion and the anchor portion defining one or more apertures for receiving fasteners that attach the bone plate to bone; and
a thumbscrew including a graspable handle portion affixed to an elongated shaft portion, the shaft portion having an external thread and also having a distal end configured to contact bone, the shaft portion being configured to be disposed in threaded engagement with an aperture of the arm portion via the external thread, such that the handle portion is located above an outer surface of the arm portion, and such that a leading region of the shaft portion projects from an inner surface of the arm portion, to enable support of the arm portion at a slant above a bone surface by the thumbscrew and the fulcrum portion of the bone plate,
wherein the thumbscrew is marked to identify an angle of slant at which the thumbscrew supports the arm portion.

2. The system of claim 1, wherein the graspable handle portion is cylindrical.

3. The system of claim 1, wherein the graspable handle portion includes a knurled surface region.

4. The system of claim 1, wherein the graspable handle portion is elongated in a direction parallel to the long axis of the thumbscrew.

5. The system of claim 1, wherein the thumbscrew is a first thumbscrew, the system further comprising a second thumbscrew, wherein the first and second thumbscrews have shaft portions of different length from one another.

6. The system of claim 5, wherein each of the first and second thumbscrews is marked to identify an angle of slant at which the thumbscrew supports the arm portion.

7. The system of claim 1, wherein the anchor portion has an inner surface that is contoured to match a surface region near an end of a bone, such that the anchor portion fits onto the surface region.

8. The system of claim 7, wherein the anchor portion has an inner surface that is contoured to match a surface region near a distal end of a radial bone.

9. The system of claim 1, wherein the bone plate has a bend that renders an outer surface of the bone plate at least substantially concave in profile.

* * * * *